US00PP18955P3

(12) United States Plant Patent
Trezise et al.

(10) Patent No.: US PP18,955 P3
(45) Date of Patent: Jun. 17, 2008

(54) SEEDLESS GRAPE

(50) Latin Name: *Vitis vinifera*
Varietal Denomination: Chardonnay I10V1-S

(76) Inventors: Robert Garry Trezise, Box 196, Paringa, South Australia 5340 (AU); Peter Michael Burne, Box 1723, Renmark, South Australia 5341 (AU)

( * ) Notice: Subject to any disclaimer, the term of this patent is extended or adjusted under 35 U.S.C. 154(b) by 0 days.

(21) Appl. No.: 10/949,725

(22) Filed: Sep. 24, 2004

(65) Prior Publication Data

US 2005/0091720 P1 Apr. 28, 2005

(30) Foreign Application Priority Data

Sep. 25, 2003 (AU) ..... 2003905224

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

PP15,774 P3 * 5/2005 Bourne ..... Plt./205
2005/0091720 P1 * 4/2005 Trezise et al. ..... Plt./205

OTHER PUBLICATIONS

UPOV ROM GTITM Computer Database, GTI Jouve Retrieval Software 2005/03 Citation for 'I10V1–S'.*

* cited by examiner

*Primary Examiner*—Wendy C. Haas
(74) *Attorney, Agent, or Firm*—Klauber & Jackson L.L.C.

(57) ABSTRACT

The present invention relates to a seedless grape variety, which is a clone of 'Chardonnay I10V1' grape. A seedless variety has considerable advantages in wine-making in that the wine being produced can be left on the skins for longer than in the case of conventional cultivars, without developing the bitter taste associated with seeds.

3 Drawing Sheets

1

The Latin name of the genus and species of the plant claimed herein is *Vitis vinifera*. The name of the cultivar is 'Chardonnay I10V1-S'. The plant is a seedless grape variety, which is a clone of the 'Chardonnay I20V1' cultivar.

BACKGROUND OF THE INVENTION

A seedless grape has considerable advantages in wine-making in that the wine being produced can be left on the skins for longer than in the case of conventional 'Chardonnay' clones, without developing the bitter taste associated with seeds.

The improved grape of the present invention was first noticed, in January of 1999, by one of the inventors, who observed a vine having unusually small bunches with small berries in a 'Chardonnay I10V1' planting on the property/vineyard in Paringa, South Australia, Australia. On closer inspection, the 'Chardonnay I10V1' grapes were also found to be seedless.

A year later, a viticultural consultant suggested that the vine should be investigated, as it might be of value in winemaking. A test sample of two liters of wine was produced from the grapes. The wine showed potential, despite receiving insufficient attention during the winemaking process.

In the next year's vintage (2001), further tests were conducted. The grapes were found to contain 12 g/l total acid at 13.9 Be, which was a remarkable result. The grapes were made into wine in the laboratory, and this time the wine appeared very promising. The wine analysis was 8.0 g/l total acid, pH was 2.85 (remarkably good), and the alcohol content was 13.9%.

2

The mother vine of the seedless 'Chardonnay I10V1' plant was DNA typed using six microsatellite loci, and found to match the genotype of material designated as 'Chardonnay I10V1', as recorded in the databases. The seedless clone of 'Chardonnay I10V1' was designated 'Chardonnay I10V1-S.'

During the dormancy period of 2001, the 'Chardonnay I10V1-S' mother vine was tested and no vitiviruses or phytoplasmas were detected.

In spring of 2001, sufficient vines were propagated from the 'Chardonnay I10V1-S' mother vine to plant two 100-meter-long rows on Paulsen rootstock, and one row on their own roots on the property/vineyard in Paringa, South Australia, Australia (CT 5136/331 Hundred Murtho Section 66). These new vines were regularly examined, through to harvest 2004, for any variation from the mother vine. Three vines each produced an individual cane (shoot) that reverted back to the original 'Chardonnay I10V1'. These canes had normal sized berries and bunches and had normal leaves. This reversion rate is within normally accepted tolerances. All the other canes produced on the three vines remained seedless, as did all the canes on the other 190 vines.

Meanwhile, in late 2002, further trials were carried out with a planting of the 'Chardonnay I10V1-S' on a property on Nixon Road, Monash, South Australia, Australia. The trial planting was covered by a non propagation agreement.

During vintage 2003, wine was produced from the mother vine and its young progeny. The yield from the mother vine was 31 kg (equivalent to 38.5 t/ha), and winemakers examining the wine produced from the seedless grapes were favourably impressed.

During the 2004 vintage, wine was again produced from the mother and daughter seedless vines, with similar results.

BRIEF SUMMARY OF THE INVENTION

The present invention relates to a seedless 'Chardonnay I10V1' clone, namely, 'Chardonnay I10V1-S', and in particular to a seedless 'Chardonnay I10V1' having a readily apparent morphological marker. That morphological marker is a characteristic and very distinctive leaf shape, whereby the petiolar sinus forms an open "V", which serves to "fingerprint" the variety. The seedless 'Chardonnay I10V1' plant specifically described herein, 'Chardonnay I10V1-S', is a clone of 'Chardonnay I10V1', and can be readily distinguished from all other 'Chardonnay I10V1' clones by its unique leaf marker, even before examining its equally distinctive bunches and berries. It can therefore be easily identified. As far as the applicants are aware, that is not possible for any other clones of *Vitis vinifera* cultivars, and currently not even DNA analysis can distinguish between clones.

'Chardonnay I10V1-S' was originally produced from 'Chardonnay I10V1' grafted to rootstock. 'Chardonnay I10V1', also known as 'FPMS6' or 'FPMS6 Chardonnay' is sourced from Foundation Plant Material Services, University of California, Davis, U.S.A. It is readily available from nurseries. The 'Chardonnay I10V1-S' has the following characteristics:

- It has been confirmed by DNA testing to belong to the 'Chardonnay I10V1' variety.
- It produces wine with characteristic 'Chardonnay I10V1' flavours and bouquet.
- Bud bursts are in spring, at nearly the same time as known 'Chardonnay I10V1' and other clones. For example, in 2004, bud bursts for the 'Chardonnay I10V1-S' were just 6 days later than for conventional 'Chardonnay I10V1'.
- It matures at the same time as 'Chardonnay I10V1', and has the same growing habit as 'Chardonnay I10V1'.
- It produces white grapes that have the distinctive flavours that characterize 'Chardonnay I10V1' other similar varieties.
- It produces bunches that have all the hallmarks of 'Chardonnay I10V1', except that they are approximately one-third the weight (ie about 55 g, compared to about 145 g).
- It produces berries that are much smaller than 'Chardonnay I10V1' berries (ie each berry weighs around 0.44 g, as compared to a weight of around 1.3 g for 'Chardonnay I10V1').
- It produces berries that contain, in most cases, aborted seeds although, in a very small number of cases, there will be the occasional normal-sized seed. To the untrained person, they appear virtually seedless. The term "seedless", as used throughout the specification and claim, has this meaning, and does not necessarily indicate that the berries completely lack seeds.
- The leaves, although otherwise similar to 'Chardonnay I10V1' and closely related varieties, have the petiolar sinus forming a distinctive open "V" with slight parallel veining adjacent to the sinus. This enables 'Chardonnay I10V1-S' to be readily distinguished from all other 'Chardonnay I10V1' clones.

These distinctive characteristics are clearly shown in the photographs of FIGS. 1, 2 and 3. From the presence of this morphological marker, being the characteristic and very distinctive leaf shape, it can be surmised that the gene for the seedless characteristic is closely linked to that for the leaf shape marker.

The seedless gene mutation is unusual, in that the berries of 'Chardonnay I10V1-S' still set well.

The berries of the present variety 'Chardonnay I10V1-S', have a higher acid content than that of 'Chardonnay I10V1' and similar varieties at the same stage of maturity. This is a particular advantage for grapes grown in high temperature regions, where low acid content seems to be a problem.

'Chardonnay I10V1-S' tends to produce much smaller bunches and much smaller berries than other 'Chardonnay I10V1' clones. The smaller size of the berries means that there will be a higher ratio of skin to fruit volume. However, this is not a problem, because the lack of seeds means that there are still similar proportions of flesh. In fact, the higher ratio of skin to fruit volume can be advantageous, in that some significant flavour components are mainly present in the vicinity of the skin.

DETAILED BOTANICAL DESCRIPTION

Various tests have been carried out to characterise 'Chardonnay I10V1-S'.

Firstly, the morphological characteristics have been observed.

Figure 1:
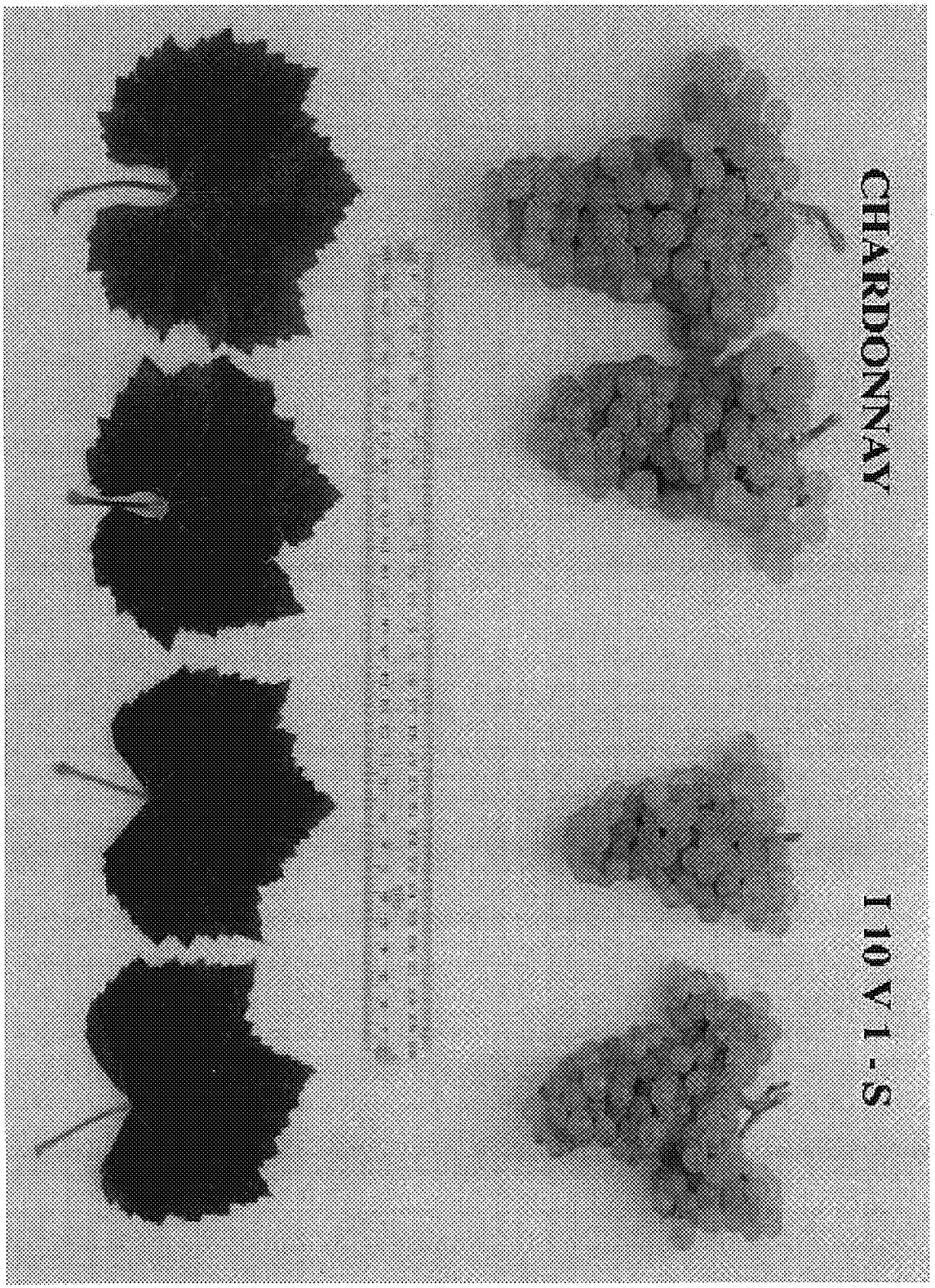
FIG. 1 is a side-by-side comparison of bunches of 'Chardonnay I10V1' grapes, and the leaves of that variety, with bunches of 'Chardonnay I10V1-S', and the leaves of this new clone. ('I10V1' is the Australian code for 'FPMS6'.)
Figure 2:
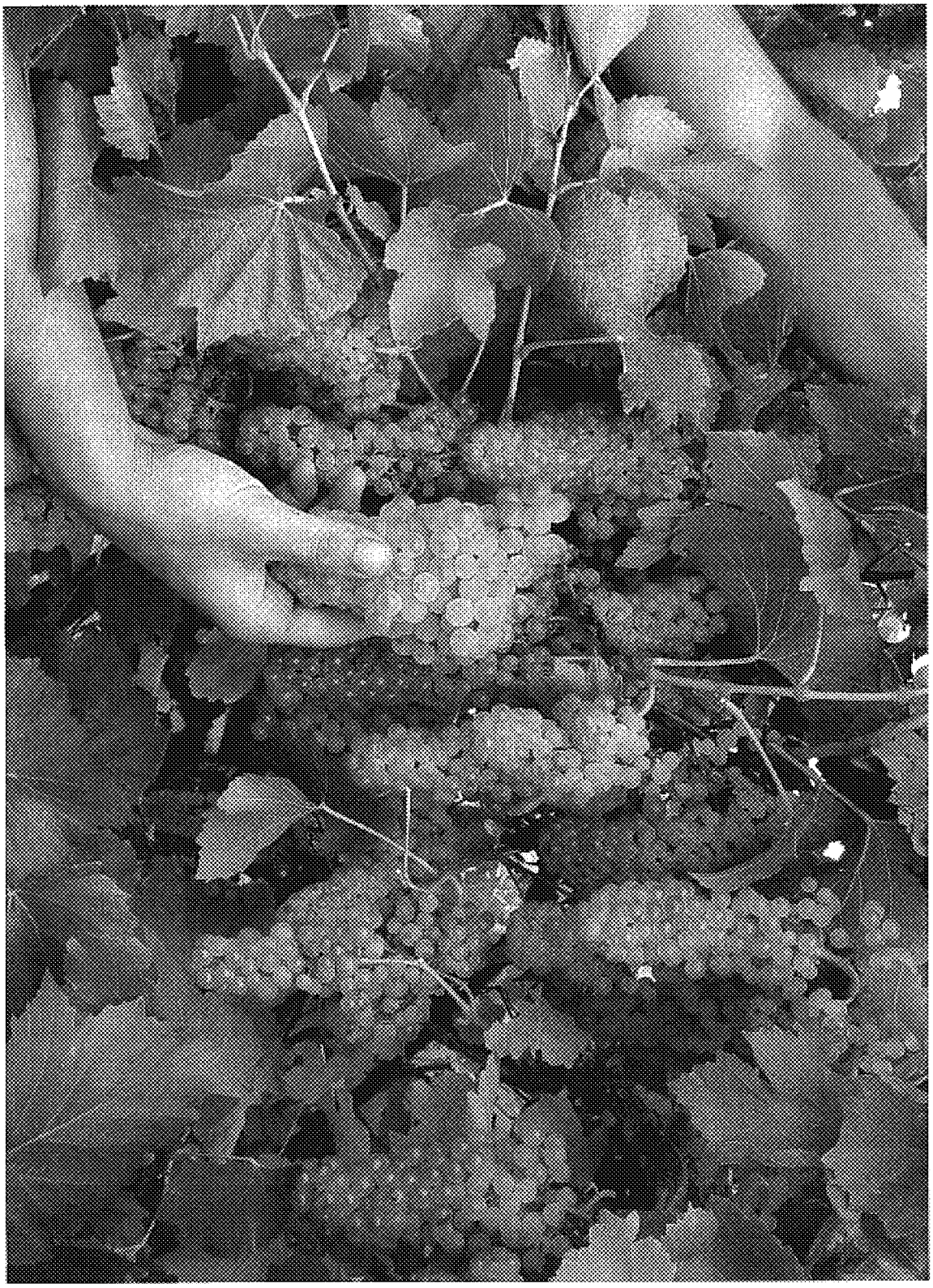
FIG. 2 is a comparison of a bunch and leaf of 'Chardonnay I10V1-S' (foreground) with bunches and leaves of a 'Chardonnay I10V1' vine (background).
Figure 3:
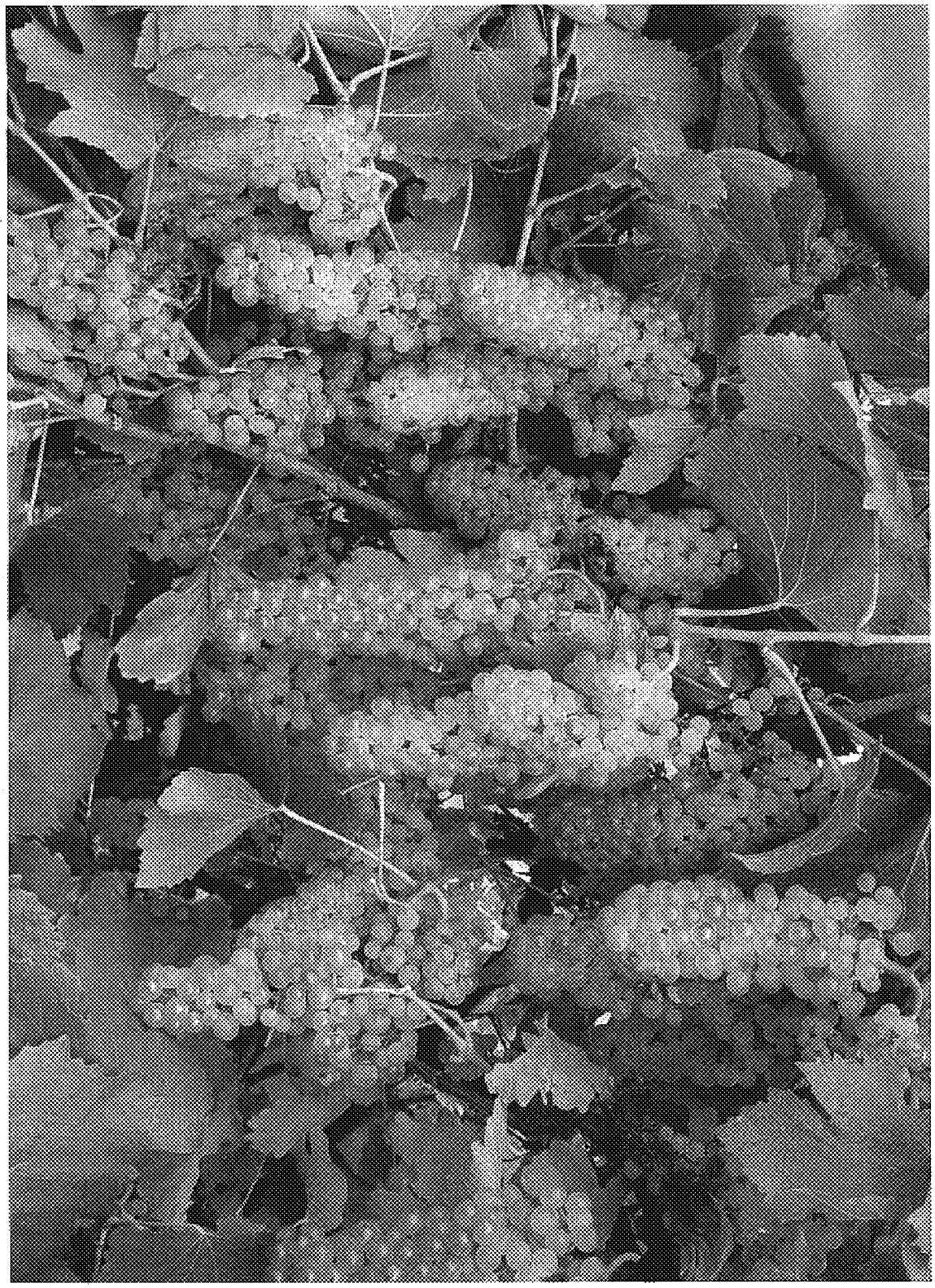
FIG. 3 is a photograph of 'Chardonnay I10V1-S'.

Most significantly, there is a morphological marker, being the distinctive and characteristic leaf shape. This is shown in FIG. 1, where the leaf shape of 'Chardonnay I10V1-S', is compared to that of the parent variety ('Chardonnay I10V1'). The petiolar sinus of the leaf of 'Chardonnay I10V1-S' is a distinctive open "V" with slight parallel veining adjacent to the sinus.

'Chardonnay I10V1-S' has the same growing habit as 'Chardonnay I10V1', and produces bunches of white grapes which have all the hallmarks of 'Chardonnay I10V1' and similar varieties, except that the bunches are approximately one-third the weight (ie around 55 g, compared to around 145 g). The berries are much smaller than 'Chardonnay I10V1' berries (ie about 0.44 g, as compared to about 1.3 g). The berries appear to be virtually seedless.

A sample of 'Chardonnay I10V1-S' was DNA typed using six microsatellite loci. Its DNA profile was compared with DNA profiles of other grapevine material contained in a database of the testing laboratory. The source grapevine material used to produce the database was drawn from collections held by South Australian State and Australian National Varietal Collections. This material, in turn, was originally received from overseas countries, together with a description of the material as representing a certain named variety of grapevine. Subsequently, most of that material was subject to independent expert ampelographic verification. The genotype of 'Chardonnay I10V1-S' was found to match the genotype of the material designated as 'Chardonnay I10V1' in the database.

Samples of 'Chardonnay I10V1-S', supplied as dormant canes, were PCR tested for the presence of the following viruses and phytoplasmas: grapevine leafroll-associated viruses 1 to 5, Rupestris stem pitting associated viruses 1 and 2, Grapevine Vitiviruses A, B and D, grapevine fleck viruses A and B, Grapevine Fanleaf virus and phytoplasmas (including Australian Grapevine Yellows). None were detected.

The berries of 'Chardonnay I10V1-S' were found to have a lower pH than 'Chardonnay I10V1' at the same stage of maturity.

Because the berries are virtually seedless, less tannins are present. The berries also have a relatively low phenolic content.

During the 2002 vintage, a winemaking trial was conducted, in which 'Chardonnay I10V1-S' and 'Chardonnay I10V1' variety were compared. The trial yielded the following data.

Fruit weight (total delivered):
*Seedless.*—33.65 kg.
*Seeded.*—119.35 kg.
Bunch weight (based on a sample of 62-77 bunches):
*Seedless.*—69.48 g.
*Seeded.*—113.71 g.
Berry weight (based on a sample of 195-198 berry bunch):
*Seedless.*—0.483 g.
*Seeded.*—1.149 g.
Extraction rate (NB: Pressing was conducted using a water bag press applying a pressure of 225 kPa — greater extraction rates would probably be achievable under commercial conditions using greater quantities of fruit):
*Seedless.*—594 L/tonne (unclarified following pressing). 535 L/tonne (clarified following racking).
*Seeded.*—595 L/tonne (unclarified following pressing). 536 L/tonne (clarified following racking).
Juice analysis (NB: Fruit was stored at 0° C. for a period of 72 hours prior to crushing. A substantial amount of tartaric acid may have been lost during this period tut to potassium bitartrate precipitation):
*Seedless.*—Total Soluble Solids=23.0° Brix, 12.8° Baume. pH=3.16. Titratable Acidity=6.6 g/L as tartaric acid.
*Seeded.*—Total Soluble Solids=23.4° Brix, 13.0° Baume. pH=3.38. Titratable Acidity=4.58 g/L as tartaric acid.

Mature Leaves of the plant have the following characteristics: Average blade length — 8 cm, Average blade width — 10.1 cm, Size of blade — Medium, Shape — Orbicular, Anthocyanin colouration of main veins on upper side of the blade — Absent to very weak, Mature leaf profile — Wavy, Blistering surface of blade upper surface — Weak, Leaf blade tip — in the plane of the leaf, Margins — Slightly lobed, Apex — Acuminate, Base — Wide open, Thickness — Medium, Undulation of blade between main and lateral veins — Small, Shape of teeth — Mixture of straight sides with points and slightly convex with points, Length of the teeth — 2-8 mm, Ratio of length/width of teeth — about 0.7:1, General shape of petiole sinus — Wide open, Tooth at petiole sinus — Absent, Petiole sinus limited by veins — Present, Shape of upper lateral sinus — Open, Prostrate hairs between veins on lower surface of blade — Absent to very sparse-sparse, Erect hairs between veins on lower surface of blade — Absent, Prostrate hairs on main veins on lower surface of blade — Sparse, Density of hairs on main veins on lower surface of blade — Sparse to medium, Prostrate hairs on main veins on upper surface of blade — Absent.

The Upper surface of the leaves have a Summer color — YG 136 A, Autumn color — YG 153 B (as classified by the RHS color chart, 1995 version), Surface texture — Slightly ribbed (slight thickening along the veins), Surface appearance — Slightly shiny, and Goffering of blade — Absent. The Lower surface of the leaves have a Summer color — YG 146B, Autumn color — YG 151A (as classified by the RHS color chart, 1995 version), Anthocyanin coloration of main veins on lower leaf surface — Absent to very weak, Glossiness — Low, Pubescence — Absent to very sparse, Surface texture — Smooth, and Surface appearance — Dull. The Petiole has the following characteristics: Length of petiole — Average approx 5 cm (3-8 cm), Length of petiole compared to middle vein — Shorter, Density of prostrate hairs on petiole — Absent, Density of erect hair on petiole — Absent, Shape of base of petiole sinus — Open, Diameter — Approx 2 mm, and Color — G 142 B with mild RP 60C tinge and striping.

The Tendrils have the following characteristics: Number: Forming at approximately 66% of nodes after the fourth node, Length — 7-15 cm, Diameter — 2-3 mm at base, Texture — Smooth, and Color — YG 145A (as classified by the RHS color chart, 1995 version).

The Woody Shoot of the plant is characterized as following. The Canes have the following characteristics: Shape — Circular to broadly elliptical in cross section, Internode length — About 5.5 cm, Width of node — About 1.2 cm, Cross section — Circular, Surface — Smooth to slightly striate, Main color — Green with red stripes, Lenticels — Inconspicuous, Erect hairs on nodes — Absent, Erect hairs on internodes — Absent, Growth of axillary shoots — Slight to moderate, 1-4 per cane. The Laterals have the following characteristics: Shape — Circular to broadly elliptical, Number — Slight to moderate, 1-4 per cane, Length — Usually less than 15 cm, Diameter — 1-3 mm, Internode length — 2.5-5 cm, and Color — GO 166C (as classified by the RHS color chart, 1995 version). The Buds have the following characteristics: Shape — Conical, Cane bud fruitfulness — Basal buds fruitful, 1-2 clusters per shoot, Length — 4 mm, Width — 5 mm, Color — GO 166B, Time of bud burst — Early (Sep. 02, 2004, Paringa, Australia).

The Flowers of the plant are characterized as follows: Flower sex — Length of first inflorescence — Position of first flowering nodes — No. 3 node, Number of inflorescences per shoot — 2, Date of full bloom — Nov. 2, 2004 (Paringa, Australia).

The Fruit of the plant have the following characteristics: Ripening period — Early, about the same as Chardonnay, Date of ripening — Late January (Paringa, Australia) for sparkling base, Late February (Paringa, Australia) for still wine, Use — Wine (both sparkling base and still wine), Keeping quality — Good, Resistance — Insects: typical of *Vitis Vinifera,* Diseases typical of *Vitis Vinifera,* Date of first harvest — Jan. 25, 2005 (for sparkling base), Refractometer test — 20.7 brix, Titratable acidity — 9.8 grams per liter (Usually approximately 2.0 g/l greater than Chardonnay at the same maturity), pH — 3.1. The Cluster has the following characteristics: Bunch size — Very small, Bunch length (peduncle excluded) — Average about 10.5 cm, Bunch width — Average about 3.6 cm, Bunch weight (natural) — Average 65 grams, Bunch density — When fully set, very dense, Number of berries — 136 average, and Form — Cylindrical, some with wings. The Peduncle has the following characteristics: Length of peduncle — Approximately 1.5 cm, Lignification of peduncle — Medium, Color — GO 165B (as classified by the RHS color chart, 1995 version). The Berry has the following characteristics: Size — Very small, Uniformity of size — Uniform, Berry weight — Average about 0.45 grams, Shape — Circular to slightly obulate, Presence of seeds — Usually only aborted seed traces but occasionally very small seed, Cross section — Circular, Dimensions — Longitudinal axis approximately 6.0 mm. Horizontal axis approximately 5.5 mm, Skin color (without bloom) — YG 150C (as classified by the RHS color chart, 1995 version), Coloration of flesh — Translucent, YG 150D (as classified by the RHS color chart, 1995 version), Juiciness of flesh — Very juicy, Berry firmness — Medium, Particular flavor — Chardonnay, Bloom (Cuticular wax) — Medium, Pedicel length — 2.5-3.0 mm, Berry separation from pedicel — Moderate. The Skin has the following characteristics: Thickness — Medium thin, Texture — Tender, Reticulation — Absent, Roughness — Absent, Tenacity — Tenacious to flesh, Tendency to crack — Resistant.

It is claimed:

1. A new and distinct variety of seedless grape plant named 'Chardonnay I10V1-S', substantially as illustrated and described herein.

* * * * *